(12) United States Patent
Kim et al.

(10) Patent No.: US 11,428,640 B2
(45) Date of Patent: Aug. 30, 2022

(54) URINE TEST DEVICE

(71) Applicant: CHUNGDO PHARM Co., Ltd, Chuncheon-si (KR)

(72) Inventors: Sung Jin Kim, Seoul (KR); Seung Jin Lee, Seoul (KR)

(73) Assignee: CHUNGDO PHARM Co., Ltd, Chuncheon-si (KR)

( * ) Notice: Subject to any disclaimer, the term of this patent is extended or adjusted under 35 U.S.C. 154(b) by 163 days.

(21) Appl. No.: 17/103,948

(22) Filed: Nov. 25, 2020

(65) Prior Publication Data
US 2022/0099583 A1    Mar. 31, 2022

(30) Foreign Application Priority Data
Sep. 29, 2020    (KR) .................. 10-2020-0126456

(51) Int. Cl.
*G01N 21/78* (2006.01)
*G01N 33/493* (2006.01)
*G01N 21/77* (2006.01)

(52) U.S. Cl.
CPC ............ *G01N 21/78* (2013.01); *G01N 33/493* (2013.01); *G01N 2021/7759* (2013.01); *G01N 2021/7773* (2013.01)

(58) Field of Classification Search
CPC .................. G01N 21/78; G01N 33/493; G01N 2021/7759; G01N 2021/7773; G01N 21/8483; A61B 5/14507; A61B 5/0059; A61B 5/1455; A61B 5/20; A61B 10/007; A61B 2010/0006
See application file for complete search history.

(56) References Cited

U.S. PATENT DOCUMENTS

2017/0102402 A1* 4/2017 Kusuhara .................. B01L 9/52

* cited by examiner

*Primary Examiner* — Jennifer Wecker
*Assistant Examiner* — Alea N. Martin
(74) *Attorney, Agent, or Firm* — Revolution IP, PLLC

(57) ABSTRACT

A urine test device includes a case in which a guide is formed, a strip tray including a strip moving body formed to be slidably movable through the guide, a plurality of strip seating parts formed on the strip moving body, and a strip fixing part configured to fix the strip seated on each of the plurality of strip seating parts, a tray movement driving part configured to slidably move the strip tray, a sensing module supported by the case and including a plurality of light-emitting diodes (LEDs) configured to emit white light for testing toward the plurality of moving strips from above the plurality of strips and a plurality of image sensors configured to detect colors of the plurality of strips, and a control part configured to control the tray movement driving part to move the strip tray.

7 Claims, 12 Drawing Sheets

[Fig 1]
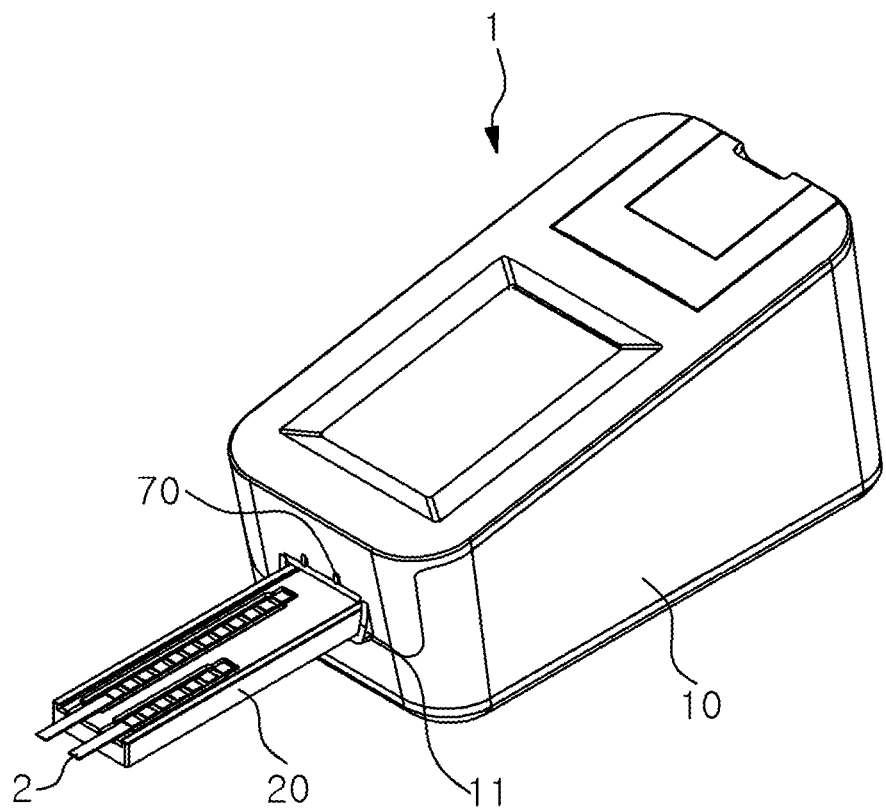

[Fig 2]
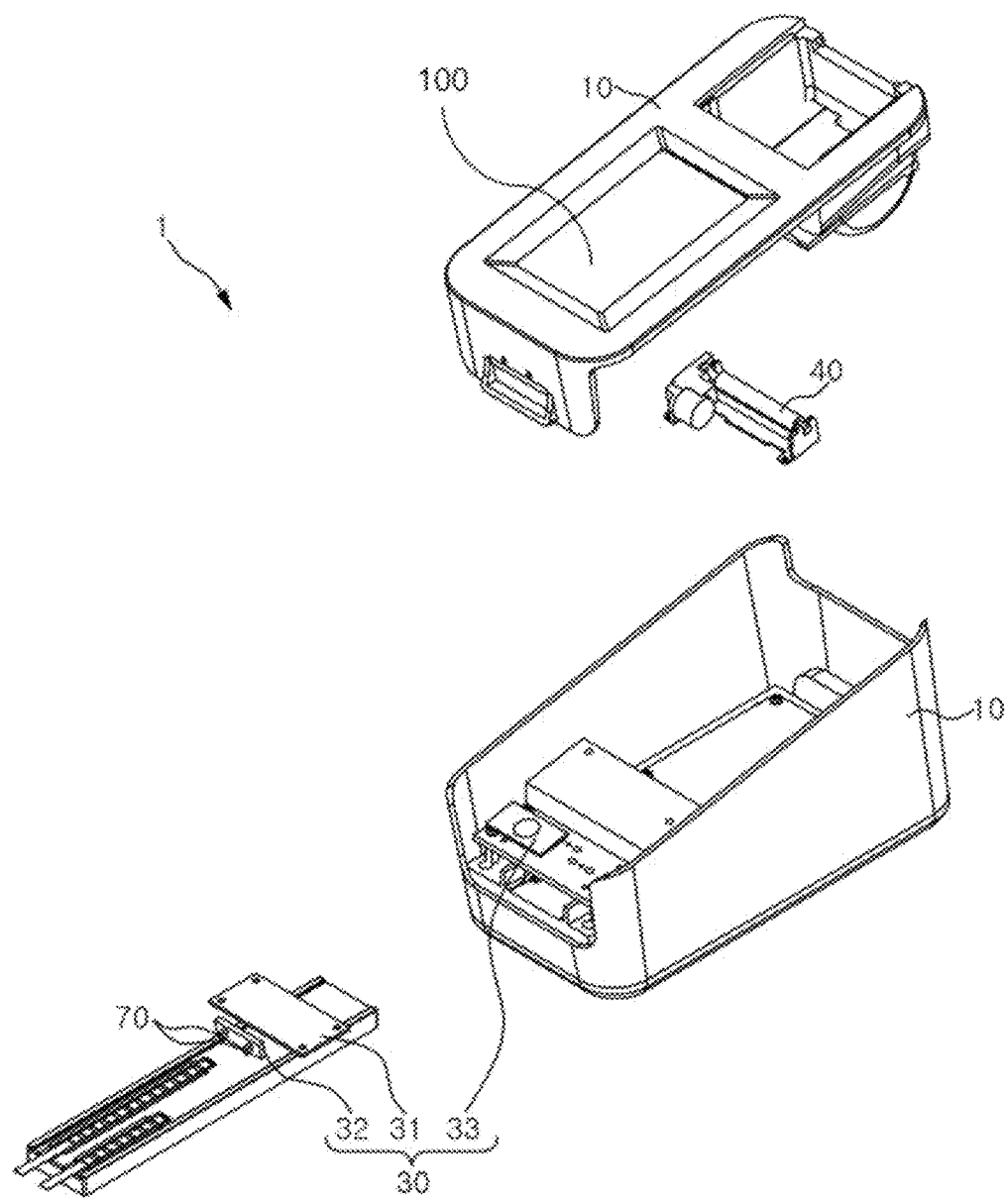

[Fig 3]
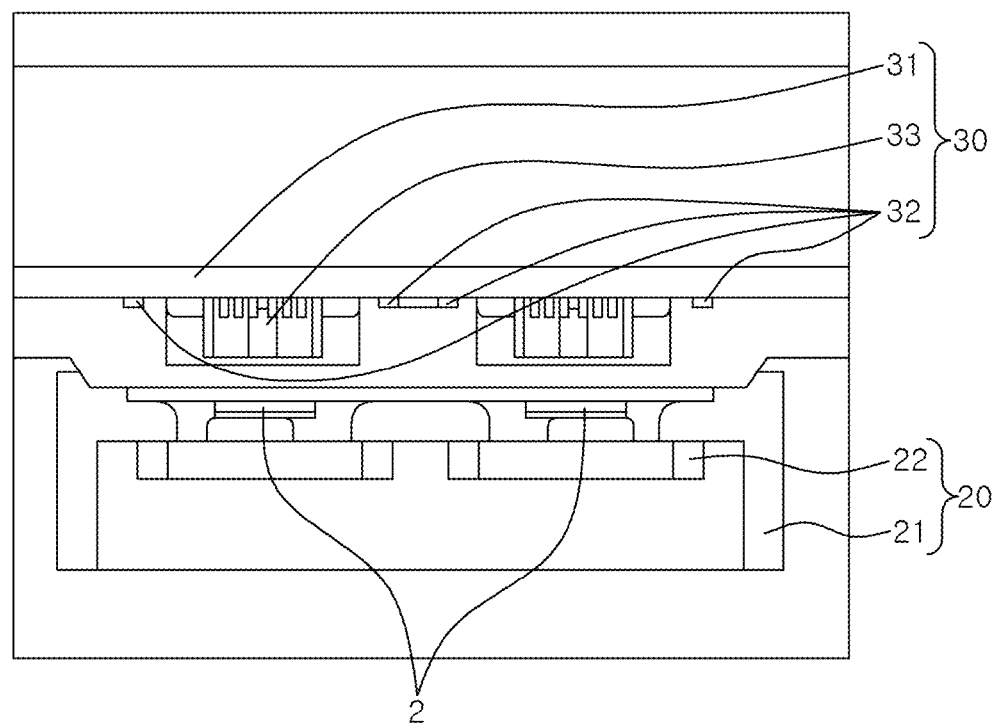

[Fig 4]
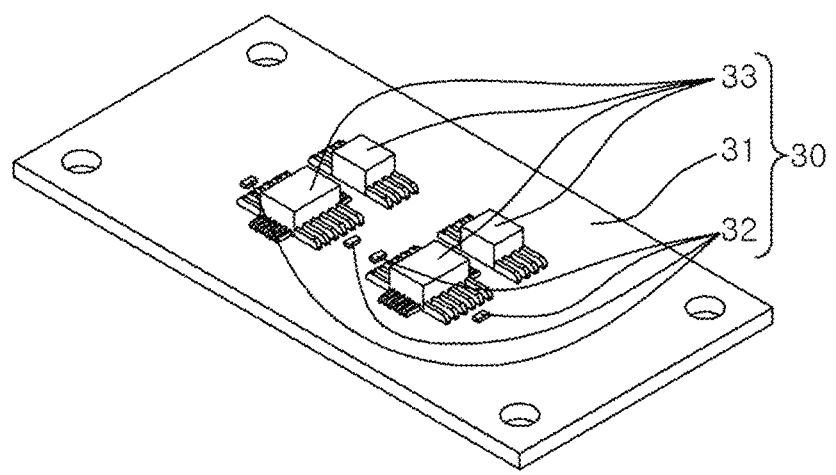

[Fig 5]
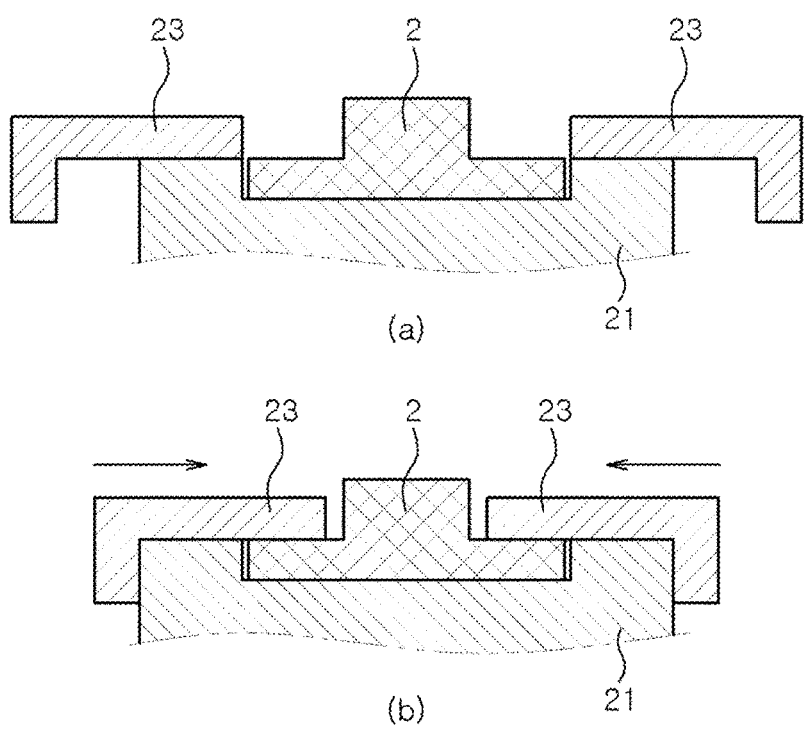

[Fig 6]
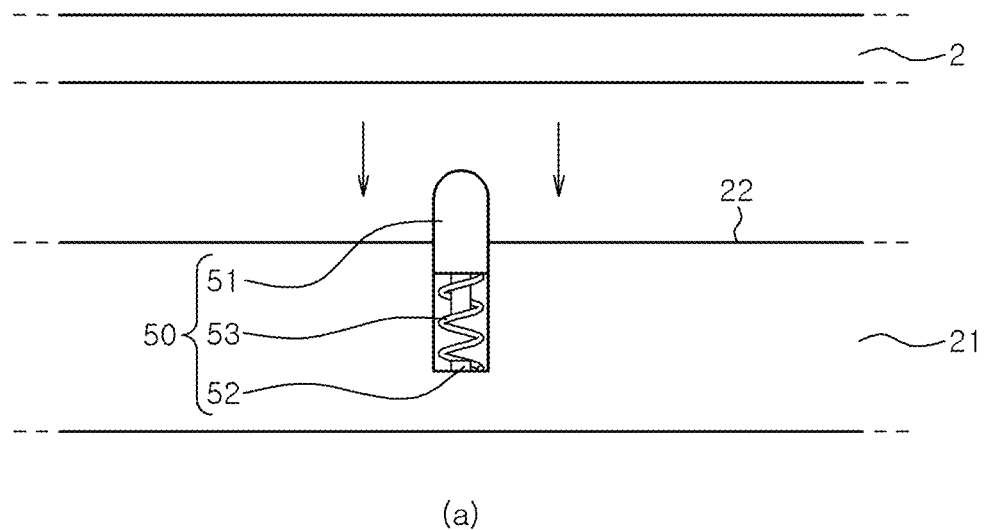
(a)
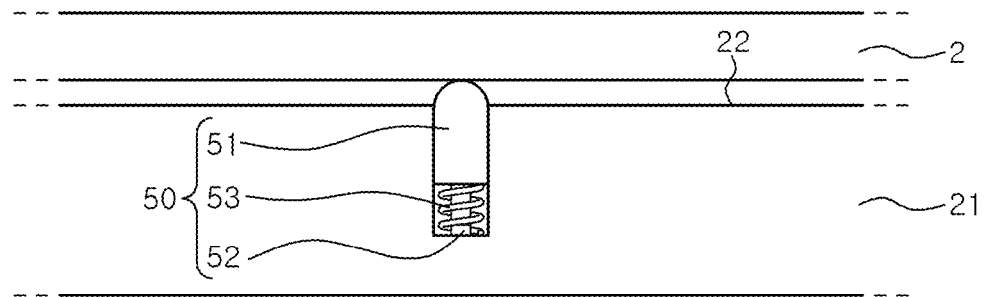
(b)

[Fig 7]
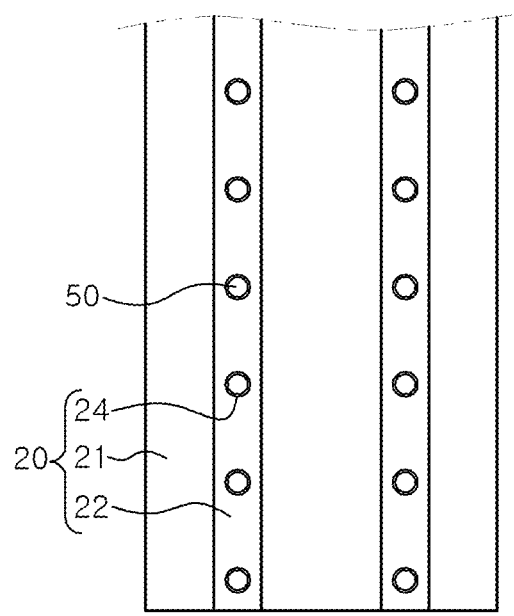

[Fig 9]
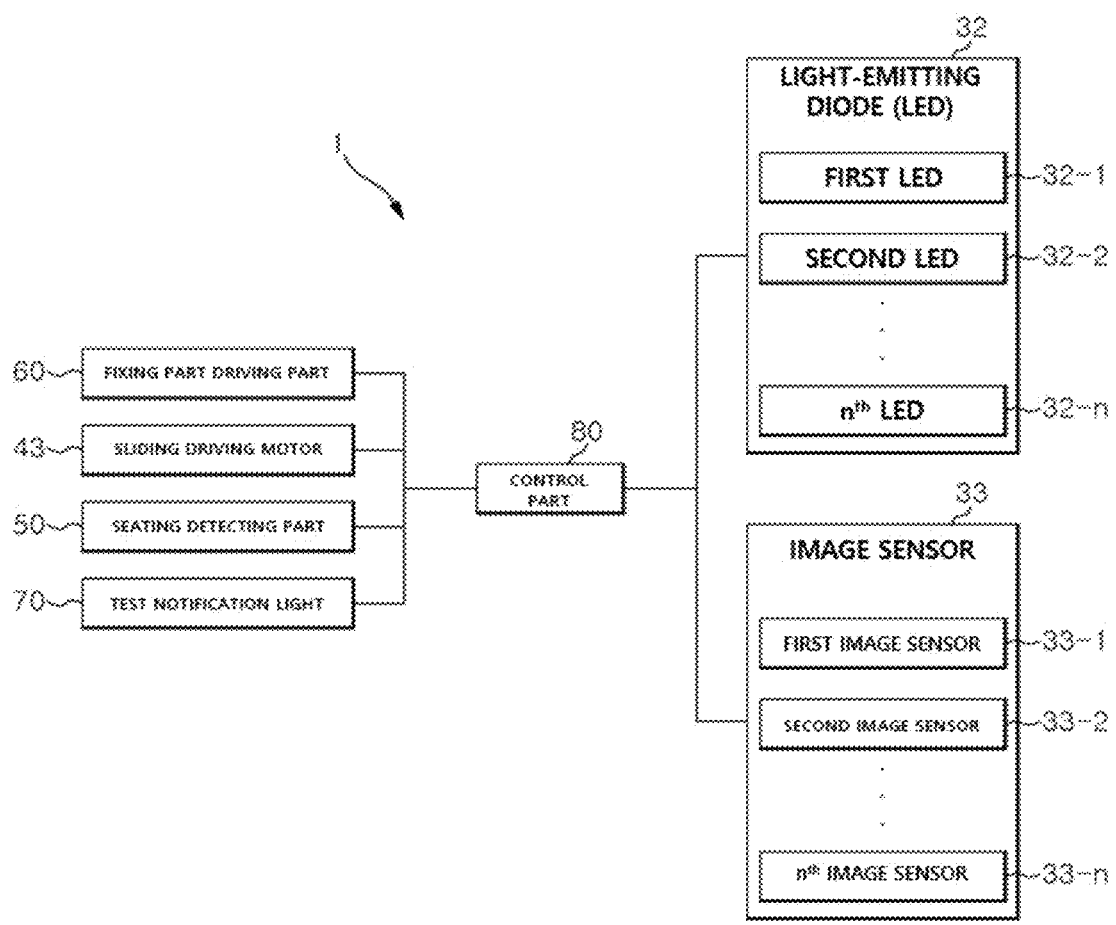

[Fig 10]
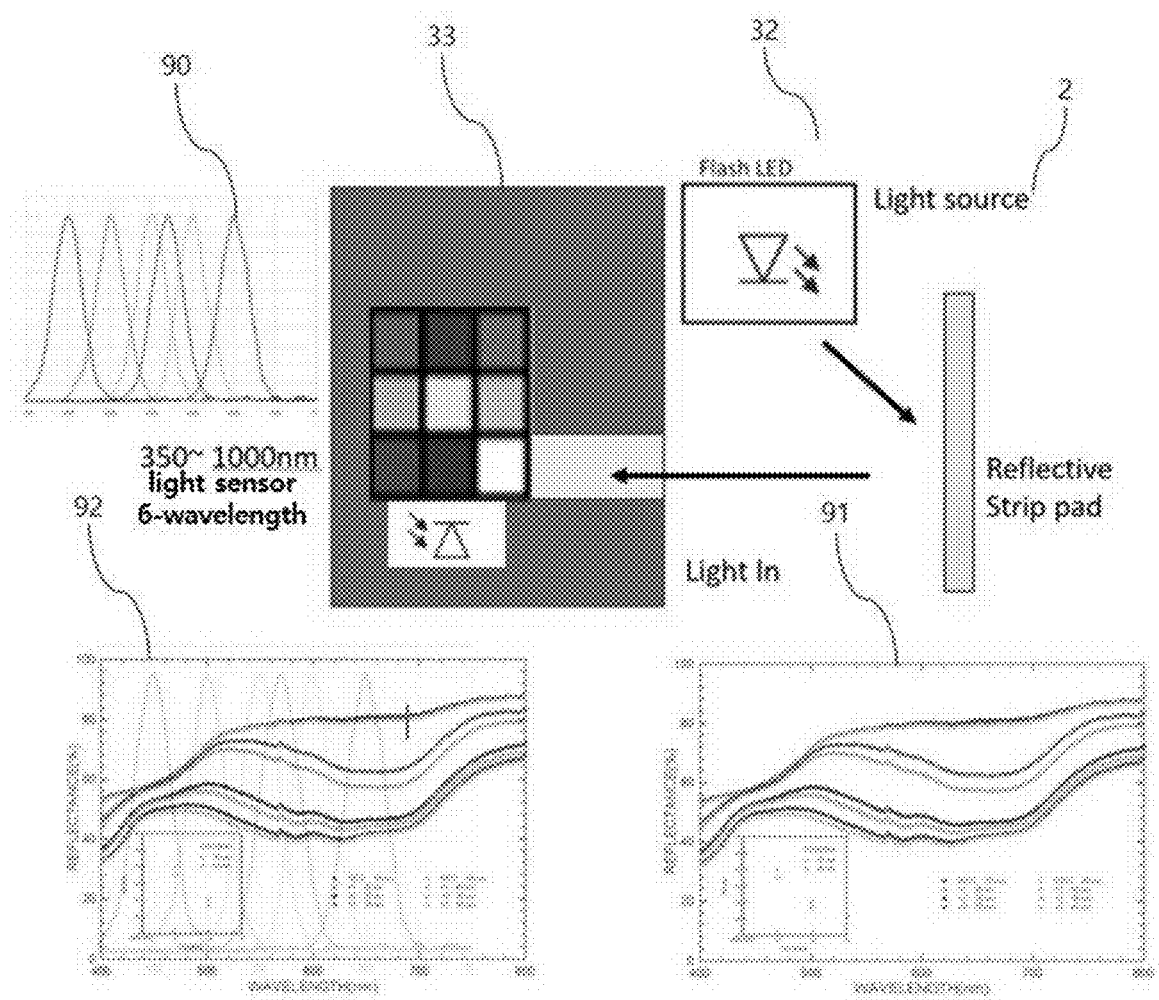

[Fig 11]
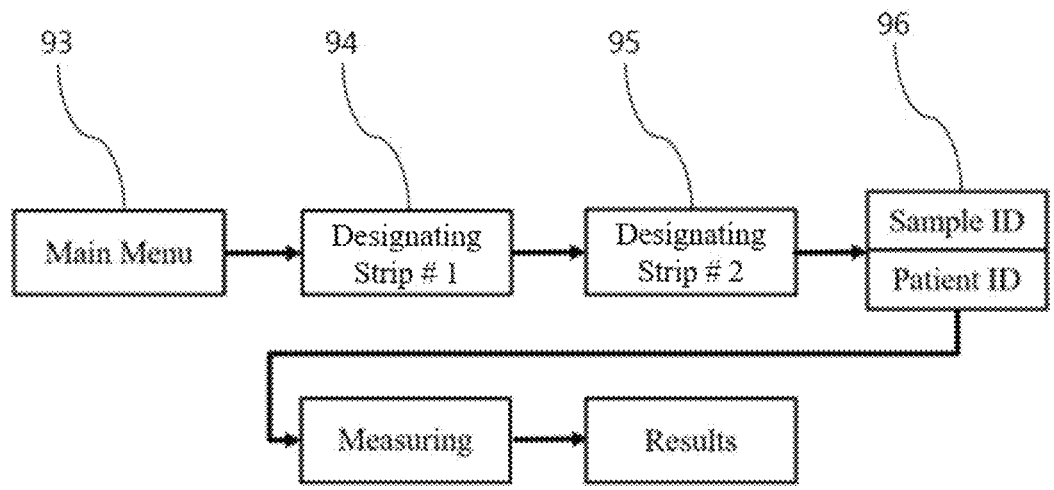

[Fig 12]
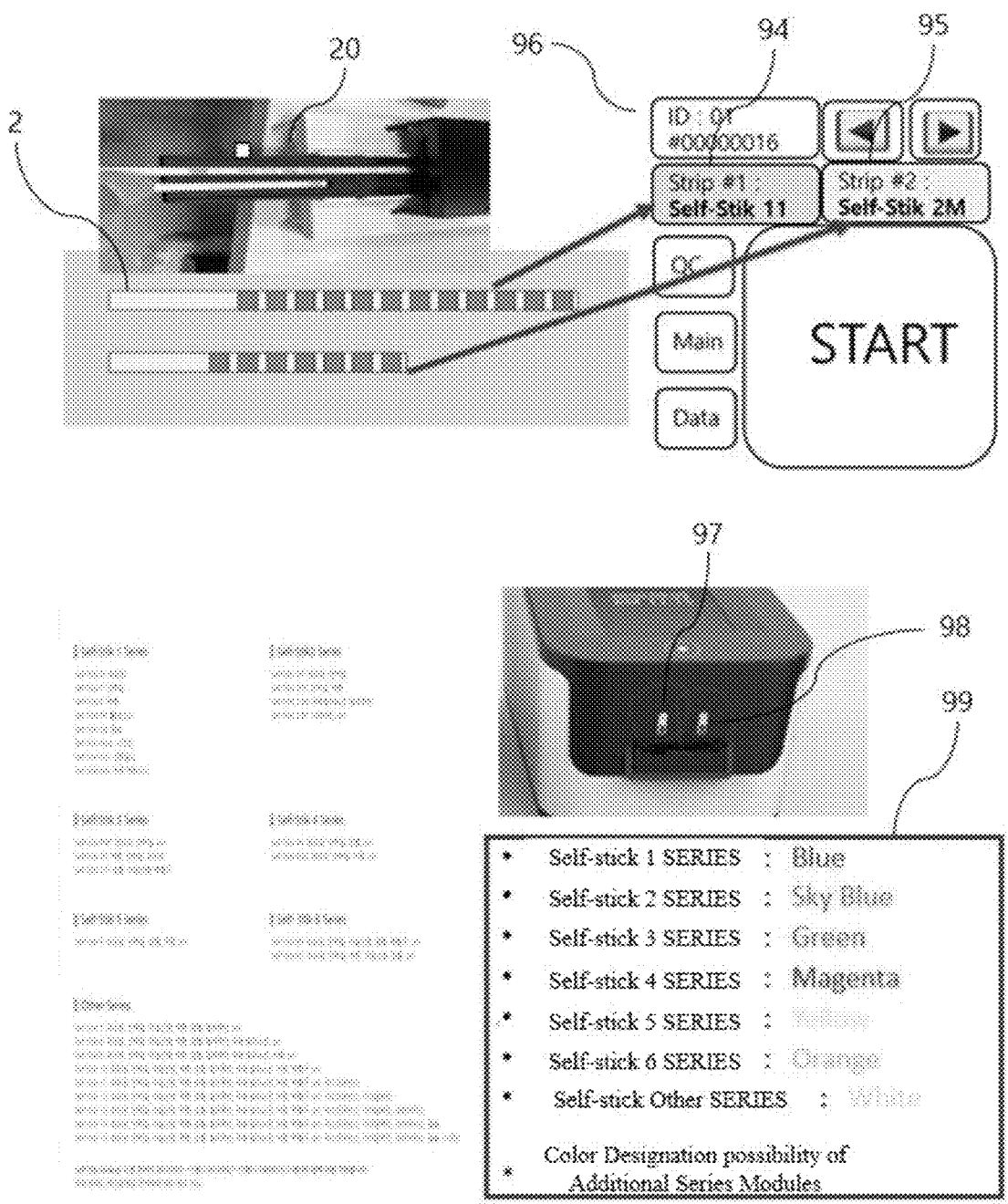

URINE TEST DEVICE

CROSS-REFERENCE TO RELATED APPLICATION

This application claims priority to and the benefit of Korean Patent Application No. KR 10-2020-0126456 filed on Sep. 29, 2020, the disclosure of which is incorporated herein by reference in its entirety.

BACKGROUND

1. Field of the Invention

The present invention relates to a urine test device, and more specifically, to a urine test device of which the number of analysis items is increased.

2. Discussion of Related Art

As demands for in vitro diagnostic test strips increase due to changing to the aging era, daily management, and personalization, urine test strips used only by professionals are expanding to be used as urine test strips for personal use. As the importance of the urine test strips, which provide a great deal of clinical data while being simple and inexpensive, is recognized, demand is increasing.

Recently, due to the diversification of test items, various diseases such as stomach cancer, colon cancer, cervical cancer, and kidney disease can be prevented using self-diagnosis, and the self-diagnosis has also been expanded to health care such as antioxidants in a body and blood vessel health measurement. Particularly, in some markets, the urine test strips which check active oxygen, microalbumin, nitric oxide, and salinity are highly preferred as healthcare products in addition to comprehensive urine test strips (Self-Stick 11 configured to check occult blood, bilirubin, urobilinogen, specific gravity, pH, nitrite, protein, leukocyte, glucose, ascorbic acid, and ketone) which are for a primary screening test.

As many as ten kinds of test papers are disposed on the urine test strip for urine test to test each test target component. In order to increase the number of the test target components, ten or more kinds of test papers are disposed on the urine test strip, and thus a length of the urine test strip is increased and it is inconvenient for a user to use the urine test strip. In addition, in order to test many test target components, two or more urine test strips should be used.

However, since the conventional urine test device is provided to test one urine test strip and two or more urine test strips should be tested per one inspectee, there are inconveniences in that the test should be repeated two times per one inspectee and analyzed results should be summarized.

SUMMARY OF THE INVENTION

The present invention is directed to providing a urine test device capable of simultaneously testing increased component analysis items.

According to an aspect of the present invention, there is provided a urine test device using strips with urine, the urine test device including a case in which a guide is formed, a strip tray including a strip moving body formed to be slidably movable through the guide, a plurality of strip seating parts formed on the strip moving body and allowing strips to be seated thereon, and a strip fixing part configured to fix the strip seated on each of the plurality of strip seating parts, a tray movement driving part configured to slidably move the strip tray in a longitudinal direction, a sensing module supported by the case and including a plurality of light-emitting diodes (LEDs) configured to emit white light for testing toward the plurality of moving strips from above the plurality of strips and a plurality of image sensors configured to detect colors of the plurality of strips to which the white light of the plurality of LEDs is emitted, and a control part configured to control the tray movement driving part to move the strip tray, control the plurality of LEDs to emit the white light toward the plurality of moving strips, and analyze urine on the basis of the colors, which are detected by the plurality of image sensors, of the plurality of strips.

The urine test device may further include a plurality of seating detecting parts configured to detect whether the plurality of strips are seated on the plurality of strip seating parts, wherein the control part may control the strip tray to be moved when the plurality of seating detecting parts detect the plurality of strips seated on the plurality of seating detecting parts.

The plurality of seating detecting parts may be disposed at positions where lengths of the plurality of strips are detectable.

The plurality of LEDs may be disposed at both sides of each of the plurality of moving strips.

The sensing module may be provided with a module substrate supporting the plurality of LEDs and the plurality of image sensors and having a plate shape, and the plurality of LEDs and the plurality of image sensors may be provided with terminals mounted on the module substrate.

The tray movement driving part may include a moving rack disposed on the strip moving body along the guide, a moving pinion engaged with the moving rack and rotated, and a sliding driving motor configured to rotatably drive the moving pinion to slidably move the strip tray in the longitudinal direction.

The image sensor may be operated using a 6-wavelength light detection method.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1 is a perspective view illustrating a urine test device according to an embodiment of the present invention;

FIG. 2 is an exploded perspective view illustrating the urine test device;

FIG. 3 is an exemplary side cross-sectional view illustrating a sensing module and a strip tray;

FIG. 4 is a detail view illustrating the sensing module;

FIG. 5 is a set of operational views of a strip fixing part;

FIG. 6 is a set of operational views of a seating detecting part;

FIG. 7 is an exemplary view illustrating arrangement of seating detecting parts;

FIG. 9 is a control block diagram;

FIG. 10 is an operational view of strip spectrometry measurement of the sensing module;

FIG. 11 is a flowchart of a program menu of the urine test device; and

FIG. 12 is a view illustrating a screen menu on which two strips are selected and a color designation table of a light-emitting diode (LED) test notification part.

DETAILED DESCRIPTION OF EXEMPLARY EMBODIMENTS

Figure 8:
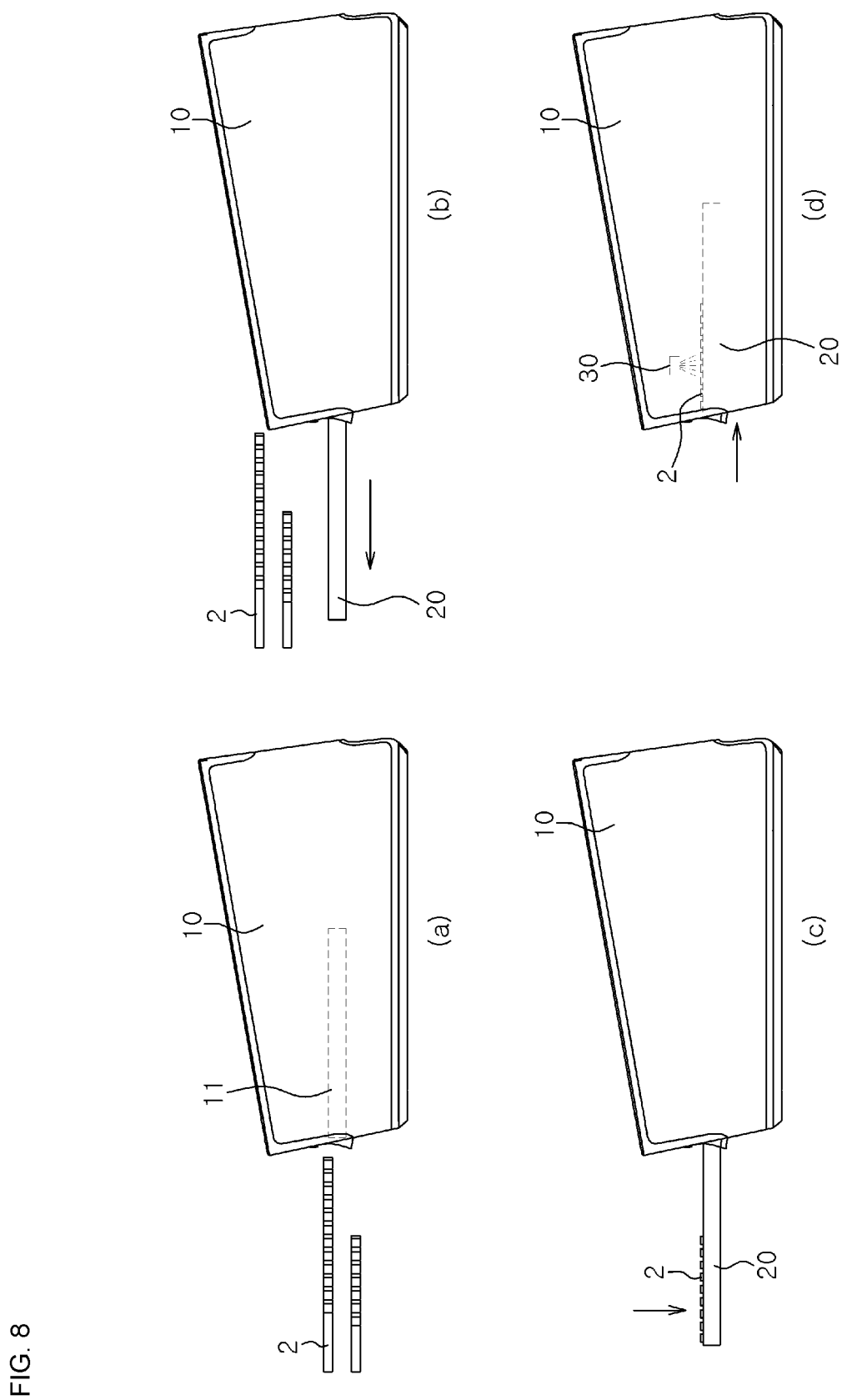
FIG. 8 is a set of test operational views of the urine test device.

Hereinafter, specific embodiments for implementing the present invention will be described in detail with reference to the accompanying drawings.

In addition, in the descriptions of the present invention, when detailed descriptions of related known configurations or functions are deemed to unnecessarily obscure the gist of the present invention, they will be omitted.

It will be understood that, when an element is referred to as being "coupled" or "fixed" to, or "in contact" with another element, it can be directly coupled or fixed to or in direct contact with another element, or intervening elements may be present.

The terminology used herein is for the purpose of describing the particular embodiments only and is not intended to be limiting to the present invention. As used herein, the singular forms "a," "an," and "the" are intended to include the plural forms as well, unless the context clearly indicates otherwise.

In addition, expressions such as "one side" and "the other side" in the present specification are described on the basis of the drawings, and when directions of the corresponding drawings are changed, the expressions can be different. For similar reasons, some components in the accompanying drawings may be exaggerated, omitted, or schematically illustrated, and sizes of the components therein do not fully reflect real sizes thereof.

In addition, although the terms "first," "second," etc. may be used herein to describe various elements, these elements should not be limited by these terms. These terms are only used for distinguishing one element from another.

The terms "comprise" and "include" used herein specify specific features, regions, numbers, steps, operations, elements, and/or combinations thereof but do not preclude the presence or addition of other specific features, numbers, regions, steps, operations, elements, and/or combinations thereof.

FIG. 1 is a perspective view illustrating a urine test device 1 according to an embodiment of the present invention, FIG. 2 is an exploded perspective view illustrating the urine test device 1, FIG. 3 is an exemplary side cross-sectional view illustrating a sensing module 30 and a strip tray 20, FIG. 4 is a detail view illustrating the sensing module 30, FIG. 5 is a set of operational views of a strip fixing part 23, FIG. 6 is a set of operational views of a seating detecting part 50, FIG. 7 is an exemplary view illustrating arrangement of seating detecting parts 50, FIG. 8 is a set of test operational views of the urine test device 1, and FIG. 9 is a control block diagram.

Hereinafter, a urine test device 1 according to the present invention will be described.

The urine test device 1 includes a case 10, a strip tray 20, a sensing module 30, a tray movement driving part 40, seating detecting parts 50, a fixing part driving part 60, test notification lights 70, and a control part 80, and a liquid crystal display (LCD) part 100 as will be described below.

The case 10 accommodates components therein and forms an exterior of the urine test device 1. The case 10 includes a guide 11 formed to allow the strip tray 20 to slidably move, enter, and exit the case. The guide 11 may slidably support the strip tray 20 from an entrance allowing the strip tray 20 to enter and exit.

Strips 2 may be seated on the strip tray 20 and moved for urine test. The strip tray 20 includes a strip moving body 21, strip seating parts 22, strip fixing parts 23, and detecting part accommodation grooves 24.

The strip moving body 21 is formed to have a long rod shape to be slidably movable through the guide 11. The strip moving body 21 may have an upper surface on which the strips 2 are loaded and sidewalls protruding upward from edges of the upper surface.

The strip seating part 22 is formed as a recessed region in which the strip 2 may be seated on the strip moving body 21.

The strip fixing part 23 is formed to fix the strip 2 seated on each of the plurality of strip seating parts 22. The strip fixing part 23 may fixedly cover an upper surface of each of the strips 2, each of which is seated on one of the plurality of strip seating parts 22 from both sides thereof. The strip fixing part 23 may be manually operated by a user or automatically driven by a driving part.

The detecting part accommodation groove 24 is a groove in which the seating detecting part 50 is accommodated. The detecting part accommodation grooves 24 may be formed in a width direction and formed perpendicular to a plate surface direction of a bottom surface of the strip seating part 22.

The sensing module 30 may check components contained in urine of the user through color, which is changed by the urine, of the test paper 2-1 of the strip 2. The sensing module 30 is supported by the case 10 and includes a module substrate 31, light-emitting diodes (LEDs) 32, and image sensors 33.

The module substrate 31 is formed in a plate shape supporting the plurality of LEDs 32 and the plurality of image sensors 33.

The LEDs 32 may emit white light for testing toward each of the plurality of moving strips 2 from above the plurality of strips 2. The plurality of LEDs 32 may be disposed at both sides from each of the plurality of moving strips 2.

The image sensors 33 may detect colors of the test paper 2-1 of the plurality of strips 2 to which the plurality of LEDs 32 emit the white light. The image sensor 33 may be operated using a 6-wavelength light detection method.

The tray movement driving part 40 may slidably move the strip tray 20 through the guide 11 in a longitudinal direction. The tray movement driving part 40 may include a moving rack 41, a moving pinion 42, and a sliding driving motor 43.

The moving rack 41 may be disposed under the strip moving body along the guide 11.

The moving pinion 42 may be engaged with the moving rack 41 to be rotated.

The sliding driving motor 43 may rotatably drive the moving pinion 42 to slidably move the strip tray 20 in the longitudinal direction.

Although the tray movement driving part 40 may include the moving rack 41, the moving pinion 42, and the sliding driving motor 43, any part capable of performing one of various methods to slidably move the strip tray 20 in the longitudinal direction may be used as the tray movement driving part 40.

The seating detecting parts 50 may detect whether the plurality of strips 2 are seated on the plurality of strip seating parts 22. The plurality of seating detecting parts 50 may be disposed at positions where lengths of the plurality of strips 2 are detectable. The seating detecting part 50 includes an operation detecting part 51, a fixed detecting part 52, and an elastic member 53

The operation detecting part 51 is accommodated in the detecting part accommodation groove 24. From a state in which an elastic force is applied to the operation detecting part 51 by the elastic member 53 in a direction away from the fixed detecting part 52, the operation detecting part 51 may move to detect a detecting state in which the operation detecting part 51 is in contact with the fixed detecting part 52 and to detect a released state in which the operation detecting part 51 is moved away from the fixed detecting part 52. That is, the operation detecting part 51 may move to detect a state in which the strip 2 is seated and to detect a state in which the strip 2 is not seated.

The fixed detecting part 52 is fixed to a bottom of the detecting part accommodation groove 24 and comes into contact with the operation detecting part 51 to transmit to the control part 80 that the strips 2 are seated thereon.

The elastic member 53 applies the elastic force to the operation detecting part 51 to enter the released state in which the operation detecting part 51 is moved away from the fixed detecting part 52.

The fixing part driving part 60 may drive the strip fixing part 23 to fix the strip 2.

The test notification lights 70 are notification lights disposed above the guide 11 and are configured to notify whether the image sensors 33 perform a test.

The control part 80 may control the tray movement driving part 40 to move the strip tray 20, control the plurality of LEDs 32 so that the plurality of LEDs 32 emit white light toward the plurality of strips 2, and analyze urine on the basis of colors, which are detected by the plurality of image sensors 33, of the plurality of strips 2.

When the control part 80 detects that the plurality of strips 2 are seated through the plurality of seating detecting parts 50, the control part 80 may control the strip trays 20 to move.

When the control part 80 detects that the plurality of strips 2 are seated through the plurality of seating detecting parts 50, the control part 80 may also move the strip fixing parts 23 to fix the plurality of strips 2.

FIG. 5 is the set of operational views of the strip fixing part 23.

In FIG. 5A, when the strip 2 is not seated on the strip seating part 22, the strip fixing part 23 may be in an open state so that the strip 2 may be seated on the strip seating part 22. When it is determined that the strip 2 is not seated on the strip seating part 22 according to a detecting signal of the seating detecting part 50, the strip fixing part 23 may control the fixing part driving part 60 so that the strip fixing part 23 may operate to be in the open state.

In FIG. 5B, when it is determined that the strip 2 is seated on the strip seating part 22 according to a detecting signal of the seating detecting part 50, the strip fixing part 23 may control the fixing part driving part 60 so that the strip fixing part 23 may operate to be in a state in which the strip 2 may be fixed.

FIG. 6 is the set of operational views of the seating detecting part 50.

FIG. 6A is a view illustrating the state in which the strip 2 is not seated on the strip seating part 22 and the elastic force is applied to the operation detecting part 51 in the direction away from the fixed detecting part 52.

In FIG. 6B, when the strip 2 is seated on the strip seating part 22, the operation detecting part 51 comes into contact with the fixed detecting part 52, and accordingly, the control part 80 may control the strip fixing part 23 to fix the strip 2.

FIG. 7 is an exemplary view illustrating the arrangement of the seating detecting parts 50

Since the strip 2 has a predetermined length, when the seating detecting part 50 is disposed at a corresponding position of the corresponding strip seating part 22, it may be recognized that the strip 2 having the predetermined length is seated on the strip seating part 22, and the LEDs 32 and the image sensors 33 of the sensing module 30 may be properly controlled in consideration of the strip 2 having the predetermined length.

FIG. 8 is the set of test operational views of the urine test device 1.

In FIG. 8A, the plurality of strips 2 on which urine has been collected by the user are moved to the urine test device 1.

In FIG. 8B, the urine test device 1 is operated to withdraw the strip tray 20 through the guide 11.

In FIG. 8C, the plurality of strips 2 are seated on the strip seating parts 22 of the strip tray 20. Then, the plurality of strip fixing parts 23 fix the plurality of strips 2, and the strip tray 20 is slidably moved through the guide 11 in an input direction.

In FIG. 8D, while the strip tray 20 is slidably moved through the guide 11 in the input direction, the plurality of LEDs 32 emit white light toward the test paper 2-1 of the plurality of strips 2, and the plurality of image sensors 33 detect colors of the test paper 2-1. Then, components contained in the urine can be checked.

FIG. 10 is an operational view of strip spectrometry measurement of the sensing module.

The sensing module 30 may check the components contained in the urine of the user through the changed colors of the test paper 2-1 of the strips 2. Amounts of the contained components are shown as changes in color for level. The changes in color are shown as spectral wavelength characteristics. The image sensors 33 may detect the colors of the test paper 2-1 of the plurality of strips 2 to which the white light of the plurality of LEDs 32 is emitted. The image sensors 33 may check spectral wavelength characteristics 90 through the 6-wavelength light detection method. Wavelength characteristics 91 of the colors according to the components contained in the strips 2 are shown, and the image sensors 33 and the wavelength characteristics are shown in a graph 92.

FIG. 11 is a flowchart of a program menu of the urine test device.

In the test device 1, the LEDs 32 may emit white light for testing toward the plurality of moving strips 2 from above the plurality of strips 2. Strip #1 94 and strip #2 95 are designated through a menu 93 of the LCD part 100 so that the plurality of strips 2 may be disposed at both sides, and a urine test is performed according to a designated inspectee identification (ID) 96.

FIG. 12 is a view illustrating a screen menu on which two strips are selected and a color designation table of a light-emitting diode (LED) test notification part.

In the urine test device 1, Strip #1 94 and strip #2 95 are designated through the menu 93 of the LCD part 100 so that the plurality of strips 2 may be disposed at both sides. A kind of the strip 2 is displayed on the LED test notification part 70 with a strip kind designation color 99 such that the strip 2 is seated on the strip tray 20.

A modifiable embodiment will be described in addition to the above-described embodiment.

When the plurality of strips 2 are input to check components of urine of a user and the plurality of strips 2 are withdrawn, an interior of the urine test device 1 may be disinfected after the strip tray 20 is input therein. This disinfection work may be performed by cleaning, drying, ultraviolet (UV) disinfecting, alcohol disinfecting, or the like.

A cleaning cover may be provided for the cleaning such that a cleaning liquid does not come into contact with the sensing module 30, a blower may be provided for the drying, and an UV lamp may be provided for the UV disinfecting.

According to the present invention, since test papers on a plurality of urine test strips can be simultaneously detected while a strip tray on which the plurality of urine test strips are seated is slidably moved, increased component analysis items can be simultaneously tested, and thus there is an effect of improving efficiency of a urine test.

While the detailed embodiments of the present invention have been described above as the specific embodiments, these are only examples, and the present invention is not limited thereto but may be interpreted to have the widest scope according to the basic spirit disclosed in this specification. Those skilled in the art may implement patterns of shapes that are not indicated herein by combining and replacing the disclosed embodiments within a range not departing from the scope of the present invention. In addition, those skilled in the art may easily change and modify the disclosed embodiments on the basis of this specification and it will be clear that such changes or modifications are within the scope of the present invention.

What is claimed is:

1. A urine test device using strips with urine, the urine test device comprising:
   a case in which a guide is formed;
   a strip tray including a strip moving body formed to be slidably movable through the guide, a plurality of strip seating parts formed on the strip moving body and allowing strips to be seated thereon, and a strip fixing part configured to fix the strip seated on each of the plurality of strip seating parts;
   a tray movement driving part configured to slidably move the strip tray in a longitudinal direction;
   a sensing module supported by the case and including a plurality of light-emitting diodes (LEDs) configured to emit white light for testing toward the plurality of moving strips from above the plurality of strips and a plurality of image sensors configured to detect colors of the plurality of strips to which the white light of the plurality of LEDs is emitted; and
   a control part configured to control the tray movement driving part to move the strip tray, control the plurality of LEDs to emit the white light toward the plurality of moving strips, and analyze urine on the basis of the colors, which are detected by the plurality of image sensors, of the plurality of strips.

2. The urine test device of claim 1, further comprising a plurality of seating detecting parts configured to detect whether the plurality of strips are seated on the plurality of strip seating parts,
   wherein the control part controls the strip tray to be moved when the plurality of seating detecting parts detect the plurality of strips seated on the plurality of seating detecting parts.

3. The urine test device of claim 1, wherein the plurality of seating detecting parts are disposed at positions where lengths of the plurality of strips are detectable.

4. The urine test device of claim 1, wherein the plurality of LEDs are disposed at both sides of each of the plurality of moving strips.

5. The urine test device of claim 1, wherein:
   the sensing module is provided with a module substrate supporting the plurality of LEDs and the plurality of image sensors and having a plate shape; and
   the plurality of LEDs and the plurality of image sensors are provided with terminals mounted on the module substrate.

6. The urine test device of claim 1, wherein the tray movement driving part includes:
   a moving rack disposed on the strip moving body along the guide;
   a moving pinion engaged with the moving rack and rotated; and
   a sliding driving motor configured to rotatably drive the moving pinion to slidably move the strip tray in the longitudinal direction.

7. The urine test device of claim 1, wherein the image sensor is operated using a 6-wavelength light detection method.

* * * * *